United States Patent [19]
Giersch et al.

[11] Patent Number: 5,166,412
[45] Date of Patent: Nov. 24, 1992

[54] ESTERS AND THEIR USE IN PERFUMERY

[75] Inventors: Wolfgang K. Giersch, Bernex; Karl-Heinrich Schulte-Elte, Onex; Cyril Mahaim, Echichens, all of Switzerland

[73] Assignee: Firmenich S.A., Geneva, Switzerland

[21] Appl. No.: 741,027

[22] Filed: Aug. 6, 1991

[30] Foreign Application Priority Data

Aug. 28, 1990 [CH] Switzerland .................. 2799/90

[51] Int. Cl.$^5$ .................. C07C 69/16; C07C 69/28
[52] U.S. Cl. .................. 560/231; 560/249
[58] Field of Search .................. 560/249, 231

[56] References Cited

U.S. PATENT DOCUMENTS 2,410,008 10/1946 Bludworth et al. .................. 260/475
4,504,412 3/1985 Harris .................. 560/231

FOREIGN PATENT DOCUMENTS 1254198 11/1971 United Kingdom .

Primary Examiner—Jose G. Dees
Assistant Examiner—B. Frazier
Attorney, Agent, or Firm—Pennie & Edmonds

[57] ABSTRACT

The compounds of the formula

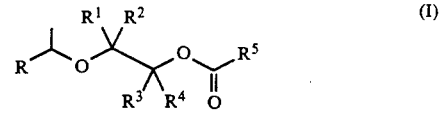

wherein R represents a 3,3-dimethyl-1-cyclopentyl or a 3,3-dimethyl-1-1cyclohexyl radical, $R^5$ represents a saturated, linear or branched, $C_1$ to $C_3$ alkyl radical and, either $R^1$ and $R^2$ stand each for a hydrogen atom, $R^3$ and/or $R^4$ representing a methyl radical, or $R^3$ and $R^4$ represent each a hydrogen atom, $R^1$ and/or $R^2$ representing then a methyl radical, are novel compounds and useful perfuming ingredients, capable of imparting to the compositions into which they are incorporated odor notes of the musky-ambrette and fruity type.

A process for the preparation of compounds (I) is disclosed.

5 Claims, No Drawings

ESTERS AND THEIR USE IN PERFUMERY

BRIEF SUMMARY OF THE INVENTION

The present invention relates to the perfume industry. It concerns, more particularly, novel compounds of formula

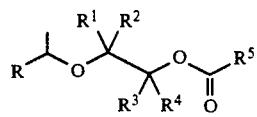

wherein R represents a 3,3-dimethyl-1-cyclopentyl or a 3,3-dimethyl-1-cyclohexyl radical, $R^5$ represents a saturated, linear or branched, $C_1$ to $C_3$ alkyl radical and, either $R^1$ and $R^2$ stand each for a hydrogen atom, $R^3$ and/or $R^4$ representing a methyl radical, or $R^3$ and $R^4$ represent each a hydrogen atom, $R^1$ and/or $R^2$ representing then a methyl radical.

Amongst compounds (I) there are cited as preferred compounds 4-(3,3-dimethyl-1-cyclohexyl)-2,2-dimethyl-3-oxapentyl propanoate, as a racemate or in the form of one of its optically active isomers of formula

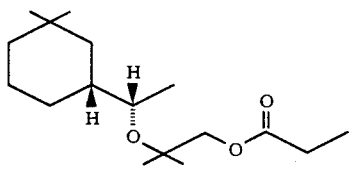

(Ie)
(+)-(1'R,4S)

or

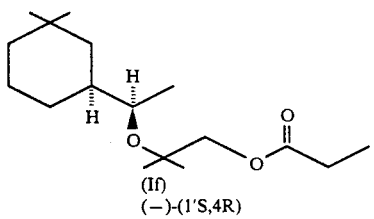

(If)
(−)-(1'S,4R)

Other preferred compounds according to the invention include 4-(3,3-dimethyl-1-cyclohexyl)-2-methyl-3-oxapentyl propanoate, 4-(3,3-dimethyl-1-cyclohexyl)-1-methyl-3-oxapentyl propanoate or any mixture thereof.

The invention also provides a mixture of compounds (I) in the form of isomers of formula

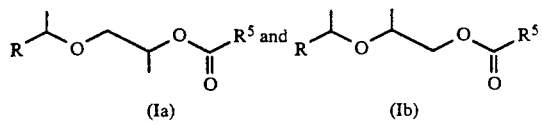

or in the form of isomers of formula

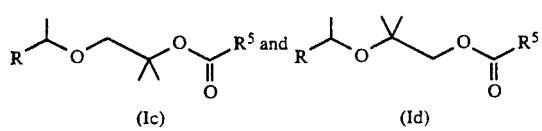

wherein symbols R and $R^5$ have the meaning indicated in formula (I).

Another object of the present invention is to provide a method to improve, enhance, confer or modify the odor properties of a perfuming composition or a perfumed article, which method comprises adding to said composition or article a fragrance effective amount of a compound of formula (I) defined above.

The invention also provides a perfuming composition or a perfumed article resulting from the above method.

A further object of the present invention is to provide a process for the preparation of a compound of formula (I) or of a mixture of compounds (I) as defined above, which process comprises treating with an appropriate esterification agent a hydroxy-ether of formula

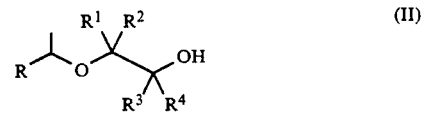

wherein symbols R and $R^1$ to $R^4$ are defined as in formula (I), or a mixture of appropriate structural isomers of formula (II).

BACKGROUND AND DETAILED DESCRIPTION OF THE INVENTION

The perfume industry is in constant need of new perfume ingredients, capable of enlarging and/or improving the palette of odor notes already available to the perfumer. The compounds of formula (I) defined above bring a new contribution to this field.

We have now discovered that compounds (I), which are novel chemical compositions, possess very useful odor properties and can therefore be used for the preparation of perfuming compositions and perfumed articles. They are, in fact, capable of developing odor notes of the musky, ambrette type, together with fruity, and sometimes floral, type characters.

The compounds according to the invention may present themselves in a pure state or in the form of a mixture of isomers, and this as a function of the nature of substituents $R^1$ to $R^4$. Thus, compounds (I) may present themselves in the form of a mixture of isomers of formula (Ia) and (Ib) as defined above, or as a mixture of isomers of formula (Ic) and (Id) as defined above. Said mixtures are also an object of the present invention. We have, in fact, observed that these mixtures were also advantageous perfuming ingredients which could be used as alternatives to their individual ingredients.

Amongst the compounds of formula (Ia) to (Id), the compounds of formula (Ib) or (Id) are cited as preferred compounds according to the invention, their odor possessing a more pronounced musk-ambrette character, neater and more elegant, than that of compounds (Ia) or, respectively (Ic).

In addition, it has also been observed that, in spite of their common musk-ambrette character, optically active isomers of the preferred compounds (Ib) or (Id) also possessed distinct odor properties and that some isomers could perform better than others.

Amongst the compounds of the invention, 4-(3,3-dimethyl-1-cyclohexyl)-2,2-dimethyl-3-oxapentyl propanoate is cited as a preferred compound. It develops a musky, ambrette odor, possessing a floral undernote and a fruity character of the pear type. This combination of ambrette and pear characters is particularly useful and quite typical of the series of compounds (I), which impart to the compositions into which they are incorporated wholly unexpected odor notes of the pear and ambrette seeds type, as is apparent from the application examples presented further on.

The fragrance effect imparted by the above-cited preferred compound of the invention is even more powerful and muskier when said compound is used in the form of one of its optically active isomers, i.e., the compound of formula

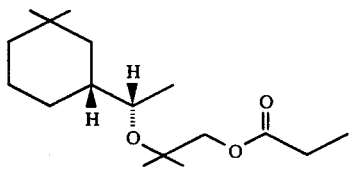

(Ie)

or (+)-(1′R,4S)-4-(3′,3′-dimethyl-1′-cyclohexyl)-2,2-dimethyl-3-oxapentyl propanoate. However, the other optically active isomers of this compound are also very useful perfuming ingredients. Likewise, the mixtures of 4-(3,3-dimethyl-1-cyclohexyl)-2,2-dimethyl-3-oxapentyl propanoate with 4-(3,3-dimethyl-1-cyclohexyl)-1,1-dimethyl-3-oxapentyl propanoate also proved to be perfuming ingredients of useful application according to the invention, having the advantage of being less costly than the preferred pure compound cited above.

Other preferred perfuming ingredients of the invention include 4-(3,3-dimethyl-1-cyclohexyl)-2-methyl-3-oxapentyl propanoate and 4-(3,3-dimethyl-1-cyclohexyl)-1-methyl-3-oxapentyl propanoate, as well as mixtures thereof. These compositions of matter developed odor notes of the musky, ambrette type, with a neat character of William pear. From an olfactive point of view, 4-(3,3-dimethyl-1-cyclohexyl)-2-methyl-3-oxapentyl propanoate is the more preferred isomer.

The odor properties of other compounds according to the invention shall be described in detail in the corresponding preparation examples presented further on.

The compounds and mixtures of the instant invention can be used with equal advantage in both fine perfumery, for the preparation of perfuming compositions and bases, and functional perfumery, for perfuming varied consumer articles. Examples of the latter include soaps, shower or bath gels, shampoos and other hair-care products, body or air deodorants. They are also useful for perfuming detergents or fabric softeners and household products.

In the above-mentioned applications, the compounds of the instant invention may be used alone or in admixture with other perfuming co-ingredients, as well as with solvents or carriers of current use in perfumery. The concentrations in which they are used can vary in a wide range of values. The man in the art knows by experience that such values are a function of the desired perfuming effect, as well as being dependent on the nature of the other co-ingredients in a given composition. By way of example, one can cite values of the order of 5 to 10%, or even 20% or more, by weight, of the compound or mixture according to the invention, relative to the weight of the composition. These values can be much lower when the compounds of the invention are used for perfuming the above-cited functional articles.

The compounds of formula (I) or their mixtures according to the invention are prepared by an original process comprising the treatment, with an appropriate esterification agent, of an hydroxy-ether of formula

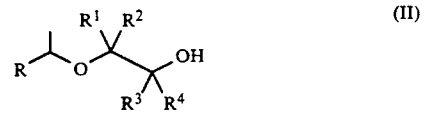

wherein symbols R and $R^1$ to $R^4$ have the meaning indicated in formula (I), or of a mixture of structural isomers of formula (II).

The hydroxy-ethers of formula (II) used as starting products in the process of the invention can be prepared from the appropriate ethanones as schematically represented hereinafter. In this scheme, symbols R and $R^1$ to $R^4$ have the meaning indicated in formula (I).

SCHEME I

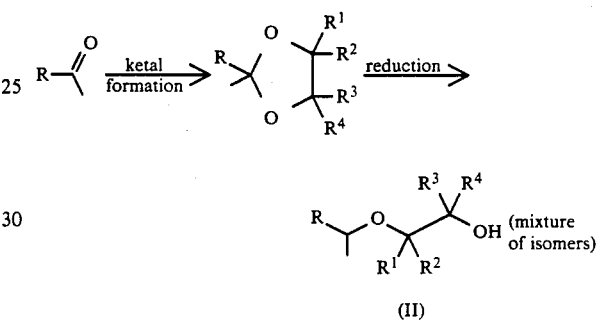

The starting ethanones in this reaction scheme, i.e., 1-(3,3-dimethyl-1-cyclohexyl)-1-ethanone or cyclademone and 1-(3,3-dimethyl-1-cyclopentyl)-1-ethanone, can be easily prepared, in the first case by known methods [see, for example, J. B. Hall et al., J. Org. Chem. 37, 920 (1972); H. R. Ansari, Tetrahedron 29, 1559 (1973)] and, in the case of the ethanone cited secondly, starting from 4,4-dimethyl-1-cyclopentene-1-carbaldehyde, as described further on.

The reactions represented in the scheme above are conventional reactions, the specific conditions of which are described in detail in the preparation examples. The reduction of the intermediate ketal represented above leads to a mixture of formula (II) isomers from which the latter can then be separated by means of the usual separation techniques such as preparative gas chromatography.

The esterification of the latter compounds, carried out under the conditions described in detail further on, makes it possible to obtain the desired formula (I) compounds.

Alternatively, the mixture of isomers (II) above-mentioned can be converted, according to the instant process, into a mixture of isomer compounds of formula (I). This mixture may be used as such in the perfumery applications according to the invention, as previously mentioned.

The compounds of formula (II) can also be obtained according to an alternative process schematically represented as follows:

SCHEME II

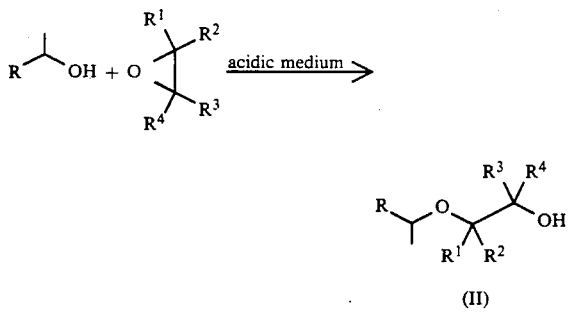

In this scheme, symbols R and $R^1$ to $R^4$ have the meaning indicated in formula (I). The process illustrated in Scheme II turns out to be more advantageous than that represented in Scheme I, because it allows the selective production of either one of the isomers of formula (Ia) or (Ib) and thus disposes of the step of isomer separation.

The starting alcohol in this process can be obtained in a conventional way from the starting ketone of Scheme I, or via other processes as described further on.

The reaction of said alcohol with the epoxide represented above is carried out in acidic medium, for example in a Lewis type acid. The specific conditions of these reactions are described in the preparation examples.

When the above-represented alcohol is used in the form of an appropriate optically active isomer, the compounds of formula (I) can then be obtained in the corresponding optically active forms, as described later on.

The invention will now be described in more detail by way of the preparation examples presented hereinafter, wherein the temperatures are indicated in degrees centigrade and the abbreviations have the usual meaning in the art.

The invention will also be illustrated by way of examples of perfumery applications of the compounds and mixtures according to the invention.

EXAMPLE 1

Preparation of
4-(3,3-dimethyl-1-cyclohexyl)-2-methyl-3-oxapentyl acetate and of
4-(3,3-dimethyl-1-cyclohexyl)-1-methyl-3-oxapentyl acetate a) Preparation of a Mixture of the Two Structural Isomers (in One Pot)

In a Schmizo type 4 l reactor, equipped with a mechanical stirrer, a water separator, a condenser, a thermometer and an introduction funnel, there were charged 200 g (1.3 mol) of cyclademone, 197.6 g of 1,2-propanediol, 500 ml of toluene and 2 g of p-toluenesulfonic acid. The mixture was heated to reflux for 8½ h, while separating the water and part of the excess of diol which also distills azeotropically with toluene. After cooling to room temperature, the reaction mixture was washed with 300 ml of brine, decanted, 100 ml of toluene added thereto and heated to reflux for 3 h with a water separator to remove the remaining water and diol.

It was then heated to 80° and 1300 ml of a solution of diisobutylaluminium hydride (DIBAH) in toluene (1.95 mol, 1.5M) were slowly added thereto. The reaction was strongly exothermic at the beginning (>100°). The introduction was accelerated, while keeping the temperature at ~90°, and completed in 2 h. The mixture was stirred for a quarter of an hour at 100°. After cooling to room temperature, 220 ml (2.16 mol) of acetic anhydride were introduced. Once 20 ml of the product had been added, the reaction stopped being exothermic and the remaining anhydride was added while heating at 60° (2 h). The reaction mixture was then heated to reflux (~110°) for 3 h. After cooling, it was poured on ice, 2 l of 10% HCl and 2 l of petroleum ether 30/50° added thereto. After neutralizing with brine, retaking the waters in petroleum ether, drying over $Na_2SO_4$, filtering and concentrating under reduced pressure, 330.3 g of raw product were obtained. The latter was distilled on residue to provide 301.6 g of a mixture containing both the desired acetates.

B. p. 100°/4 Pa; yield: 90.6%.

This mixture had a weak musky odor, with a very natural ambrette seed, pear character; curiously, the mixture was practically odorless on head sniffing, but much more powerful on the bottom notes.

b) Preparation of the Individual Isomers

A mixture of 4-(3,3-dimethyl-1-cyclohexyl)-2-methyl-3-oxa-1-pentanol and 5-(3,3-dimethyl-1-cyclohexyl)-4-oxa-2-hexanol was prepared from cyclademone, as described in the two first paragraphs of a). The mixture was then oxidated, the primary alcohol being converted into an acid and the secondary into a ketone, thus making it possible to chemically separate these two products which can then be separately treated to yield the desired acetates. It was proceeded as follows: to a solution of 43 g of pyridinium chlorochromate (PCC) in 50 ml of dimethyl formamide (DMF) there was added dropwise and under stirring a solution of 7.5 g of the above-mentioned mixture of alcohols in 50 ml of DMF. The reaction was allowed to proceed for 15 h. The mixture was then poured on 900 ml of water and extracted twice with 500 ml of ethyl ether. The combined organic layers, containing 5-(3,3-dimethyl-1-cyclohexyl)-4-oxa-2-hexanone, were washed 4 times with a diluted solution of NaOH. The organic phase was concentrated and distilled to give 1.2 g of ketone.

B. p. 150° (bath)/10 Pa.

NMR($^1$H,360 MHz): 2.1(s,C$\underline{H}_3$C=O) δ ppm.

The combined alcaline waters, admixed with ice, were acidified and the thus formed acids were extracted with ether. After bulb-to-bulb distillation, 3 g of 4-(3,3-dimethyl-1-cyclohexyl)-2-methyl-3-oxapentanoic acid were obtained.

B. p. 170° (bath)/6 Pa.

NMR($^1$H,360 MHz): 10.1(s,C(O)OH) δ ppm.

A mixture of the above-mentioned ketone with 0.1 g of LiAlH$_4$ in (C$_2$H$_5$)$_2$O was heated to reflux for 2 h. After cooling, 0.1 ml of water, 0.1 ml of 15% NaOH and 0.3 ml of water were added successively. The mixture was filtered and concentrated to yield 1.0 g of 5-(3,3-dimethyl-1-cyclohexyl)-4-oxa-2-hexanol. The latter was treated, under stirring, with 1 ml of acetic anhydride and 2 ml of pyridine for 15 h at room temperature. After having concentrated and chromatographed, 0.15 g of product containing 90% of 4-(3,3-dimethyl-1-cyclohexyl)-1-methyl-3-oxapentyl acetate and about 10% of its primary acetate isomer were obtained. A similar treatment of the above-mentioned oxapentanoic acid provided 2 g of 4-(3,3-dimethyl-1-cyclohexyl)-2-methyl-3-oxapentyl acetate in a pure form.

Analytical data: 4-(3,3-dimethyl-1-cyclohexyl)-1-methyl-3-oxapentyl acetate (4 stereoisomers).

NMR($^1$H,360 MHz): 0.87(s,3H); 0.90(s,3H); 1.07(d,J=6 Hz,3H); 1.23(d,J=6 Hz,3H); 2.05(s,3H); 3.07(m,1H); 3.34(m,1H); 3.5(m,1H); 5.02(m,1H) δ ppm.

MS: 256(M+,0), 139, 138, 123, 101, 83, 69, 55, 43.

4-(3,3-dimethyl-1-cyclohexyl)-2-methyl-3-oxapentyl acetate (4 stereoisomers).

NMR($^1$H,360 MHz): 0.88(s,3H); 0.91(s,3H); 1.07 and 1.15(d,6H); 2.07(s,3H); 3.16(m,1H); 3.66(m,1H); 4.0(m,2H) δ ppm.

MS: see above.

Odor properties: just as was the case with their mixture described in a), these two isomers develop bottom notes which are much more powerful than the headnotes. They are odor notes having the same character as that of the mixture but, in the case of the primary acetate, more powerful than the odor of the mixture. The latter also has a more pronounced ambrette character and a more elegant floral context.

EXAMPLE 2

Preparation of
4-(3,3-dimethyl-1-cyclohexyl)-2-methyl-3-oxapentyl propanoate and of
4-(3,3-dimethyl-1-cyclohexyl)-1-methyl-3-oxapentyl propanoate Into a reactor equipped with a water separator there were charged 500 g (3.2 mol) of cyclademone, 304 g (4 mol) of 1,2-propanediol, 3 l of petroleum ether 80/100° and 2 g of p-toluenesulfonic acid. The mixture was heated to reflux for 1 h. After cooling to room temperature, it was washed with 100 ml of 10% NaOH. Concentration and distillation on residue gave 670 g of 2-(3,3-dimethyl-1-cyclohexyl)-2-methyl-1,3-dioxolane.

B. p. 53°-59°/8 Pa; yield: 97.3%.

A solution of 212 g (1 mol) of the above-mentioned ketal in 500 ml of toluene was heated to 80°, under nitrogen and stirring, and a solution of 170 g (1.2 mol) of DIBAH in toluene (~800 ml of solution, 1.5M) added thereto. The introduction took approximately 2 h, with strong initial reaction exothermy. After stirring for 1 h at 100°, the reaction mixture was cooled, poured into ice and acidified with 10% HCl. After washing to neutrality, concentrating and distilling on residue, 206 g of a mixture of 5-(3,3-dimethyl-1-cyclohexyl)-4-oxa-2-hexanol and 4-(3,3-dimethyl-1-cyclohexyl)-2-methyl-3-oxa-1-pentanol were obtained.

B. p. 70°-78°/2 Pa; yield: 97.2%.

Into a reactor under stirring, there were charged 103 g (0.48 mol) of the above-mentioned mixture of alcohols, 450 ml of toluene and 79 g (1 mol) of pyridine, to which 54 g (0.5 mol) of propionyl chloride were added dropwise. The mixture was allowed to react for 3 h and then poured on ice, washed twice with 10% HCl, twice with cold 10% NaOH and twice with brine. After concentration and distillation on residue, a mixture (126 g) of the two desired propanoates was obtained.

B. p. 100°-105°/1.5 Pa; yield: 96.9%.

The two isomers were also prepared individually from the acetates described in Example 1, by way of reduction of the latter, followed by reesterification.

Analytical data: 4-(3,3-dimethyl-1-cyclohexyl)-1-methyl-3-oxapentyl propanoate (4 stereoisomers).

NMR($^1$H,360 MHz): 0.87(s,3H); 0.90(s,3H); 1.06(d,J=6 Hz,3H); 1.14(t,J=7 Hz,3H); 1.22(d,J=6 Hz,3H); 2.31(q,J=7 Hz,2H); 3.06(m,1H); 3.34(m,1H); 3.50(m,1H); 5.0(m,1H) δ ppm.

MS: 270(M+,0), 159, 139, 115, 83, 69, 57.

4-(3,3-dimethyl-1-cyclohexyl)-2-methyl-3-oxapentyl propanoate (4 stereoisomers).

NMR($^1$H,360 MHz): 0.87(s,3H); 0.90(s,3H); 1.07(t,J=5 Hz,3H); 1.05-1.18(d/t,9H); 2.35(q,J=7.5 Hz,2H); 3.12-3.22(m,1H); 3.6-3.7(m,1H); 3.94-5.09(m,2H) δ ppm.

MS: 270(M+,0), 183, 159, 139, 115, 83, 69, 57, 41.

The odor properties of these two compounds, as well as of their mixtures, are described in the introduction.

EXAMPLE 3

Preparation of
4-(3,3-dimethyl-1-cyclopentyl)-1-methyl-3-oxapentyl acetate and of
4-(3,3-dimethyl-1-cyclopentyl)-2-methyl-3-oxapentyl acetate A mixture of these two compounds was prepared by using 1-(3,3-dimethyl-1-cyclopentyl)-1-ethanone and 1,2-propanediol for the formation of the intermediate ketal and acetic anhydride in the esterification reaction, according to the process described in Example 1a) or 2, keeping the other reagents unchanged.

Analytical data of the above-mentioned mixture:

NMR($^1$H,360 MHz): 0.95(s,3H); 1.0(s,3H); 1.06-1.17(d,6H); 2.03 and 2.05(2s,3H); 3.10-3.70(m,2H); 3.94-5.03(m,2H) δ ppm.

SM: 242(M+,0), 145, 125, 109, 101, 69, 43.

Odor properties: this mixture possessed a considerably less musky odor note, harder, more pear-like and more ambrette than that of the compounds described in Example 2. The head notes were also more powerful but the odor was less tenacious on smelling strip than that of the latter.

The starting 1-(3,3-dimethyl-1-cyclopentyl)-1-ethanone was prepared thus: 2.1 g (0.088 mol) of Mg, to which a few ml of ether had been added so as to cover it, were charged into a 250 ml vessel kept under nitrogen and around ten drops of CH$_3$I were added thereto to trigger the reaction. Once the latter had started, what was left of 11.9 g of CH$_3$I (0.084 mol) in 30 ml of ethyl ether was introduced while maintaining a slight reflux. The mixture was then heated to reflux for ½ h, cooled to room temperature and 10 g (0.08 mol) of 4,4-dimethyl-1-cyclopentene-1-carbaldehyde [prepared according to Magnusson et al., J. Org. Chem. 38, 1380 (1973)], in solution in 30 ml of ether, were added thereto. It was then re-heated to reflux for 1 h. After cooling, it was poured on ice and HCl, washed to neutrality with saturated NaCl, dried, filtered and concentrated under reduced pressure. After bulb-to-bulb distillation, 6 g (yield: 53.6%) of 1-(4,4-dimethyl-1-cyclopenten-1-yl)-1-ethanol were obtained, whose analytical data were the following:

NMR($^1$H,360 MHz): 1.08(s,3H); 1.09(s,3H); 1.26(d,J=7 Hz,3H); 4.35(q,J=7 Hz,1H); 5.45(s,1H) δ ppm.

MS: 140(M+,11), 125(12), 122(23), 107(100), 91(63), 79(56), 43(21).

Into a 250 ml vessel under N$_2$ there were charged 13.2 g (60.8 mmol) of pyridinium chlorochromate in 100 ml of CH$_2$Cl$_2$ and the mixture was cooled to ~10°. A solution of 6 g (43 mmol) of the above-mentioned alcohol in 50 ml CH$_2$Cl$_2$ was added dropwise. Stirring was continued for 3 h at room temperature. The reaction mixture was poured on 200 ml of ether and filtered on a SiO$_2$ column (200 g). After concentrating under reduced pressure and bulb-to-bulb distillation (100°/12×10$^2$ Pa), 3.2 g (yield: 54%) of 1-(4,4-dimethyl-1-cyclopenten-1-yl)-1-ethanone were obtained, the analytical data of which were as follows:

NMR($^1$H,360 MHz): 1.09(s,6H); 2.3(s,3H); 2.37(s,4H); 6.64(s,1H) δ ppm.

MS: 138(M+,53), 123(100), 95(72), 67(70), 43(98).

The unsaturated ketone thus prepared (3 g, 22 mmol) was charged into a 250 ml vessel and 100 ml of acetic ether added thereto, as well as ~0.2 g of 10% Pd/C. Once vacuum had been installed, a flow of H$_2$ was passed through during 36 h (absorption ~450 ml of H$_2$). The reaction product was filtered on sintered glass, concentrated under reduced pressure and bulb-to-bulb distilled (100°/9×10$^2$ Pa) to yield 2.4 g (yield: 80%) of the desired ketone, i.e., 1-(3,3-dimethyl-1-cyclopentyl)-1-ethanone whose analytical data were the following:

NMR($^1$H,360 MHz): 0.98(s,3H); 1.02(s,3H); 2.15(s,3H); 3.02(quint,J=7 Hz,1H) δ ppm.

MS: 140(M+,7), 125(21), 97(53), 81(28), 71(41), 55(100), 43(87).

EXAMPLE 4

Preparation of
4-(3,3-dimethyl-1-cyclopentyl)-1-methyl-3-oxapentyl propanoate and of
4-(3,3-dimethyl-1-cyclopentyl)-2-methyl-3-oxapentyl propanoate A mixture of these two compounds was prepared according to the process described in Example 1a) or 2, using 1-(3,3-dimethyl-1-cyclopentyl)-1-ethanone and 1,2-propanediol to form the intermediate ketal, and propionyl chloride in the esterification reaction, the other reagents having been the same as those described in the cited examples.

Analytical data:
NMR($^1$H,360 MHZ): 0.95(s,3H); 1.0 and 1.01(2s,3H); 1.08-1.18(d+t,9H); 2.34(q,J=7.5 Hz,2H); 3.1-3.8 and 4.0(m,4H) δ ppm.

MS: 256(M+,0), 141, 125, 115, 109, 95, 81, 69, 57, 41.

Odor properties: one finds again in the odor note of this mixture the pleasant musky and ambrette character of the preferred compositions of the invention described in Example 2, with more head lift. The odor of this mixture is however finer and more powerful on the headnotes, but has less volume and is less tenaceous on a smelling strip than that of the mentioned compositions.

EXAMPLE 5

Prepration of
4-(3,3-dimethyl-1-cyclohexyl)-1-methyl-3-oxapentyl isobutyrate and of
4-(3,3-dimethyl-1-cyclohexyl)-2-methyl-3-oxapentyl isobutyrate A mixture of these two compounds was prepared according to the process described in Example 2, by reacting a mixture of 5-(3,3-dimethyl-1-cyclohexyl)-4-oxa-2-hexanol and 4-(3,3-dimethyl-1-cyclohexyl)-2-methyl-3-oxa-1-pentanol with isobutyryl chloride.

Analytical data:
B. p. 120°/20 Pa.
RMN($^1$H,360 MHz): 0.87(s,3H); 0.90(s,3H); 1.07 and 1.17(d,12H); 2.55(M,1H); 3.1-4.05(m,4H) δ ppm.
SM: 284(M+,0), 139, 129(100), 83, 71, 55, 43.

Odor properties: this mixture developed a relatively weak, musky, woody, amber, ambrette odor.

EXAMPLE 6

Preparation of
4-(3,3-dimethyl-1-cyclohexyl)-2,2-dimethyl-3-oxapentyl propanoate and of
4-(3,3-dimethyl-1-cyclohexyl)-1,1-dimethyl-3-oxapentyl propanoate The process described in Example 2 was followed, using 10 g of cyclademone and a slight excess of 2-methyl-1,2-propanediol [prepared from hydroxyacetone (Fluka) and CH$_3$MgI; NMR($^1$H,360 MHz): 1.19(s,6H); 3.4(s,2H) δ ppm; MS: 90(M+,0), 75(17), 59(100), 57(25), 43(31)] in cyclohexane, and 0,1 g of p-toluenesulfonic acid. There were obtained 14.3 g of 2-(3,3-dimethyl-1-cyclohexyl)-2,4,4-trimethyl-1,3-dioxolane (yield: 97%).

B. p. 50°/40 Pa.

NMR($^1$H,360 MHz): 0.88(s,3H); 0.92(s,3H); 1.265/1.27(2s,3H); 1.28(s,3H); 1.33(s,3H); 3.27(m,2H)δ ppm.

MS: 226(M+,0), 211(1), 168(1), 154(1), 139(2), 115(100), 69(23), 55(15), 43(61).

This ketal was treated, in an analogous manner to that described in Example 2, with 100 ml of DIBAH solution (2M in toluene). 13.2 G (yield: 90%) of a mixture of 5-(3,3-dimethyl-1-cyclohexyl)-2-methyl-4-oxa-2-hexanol (73%) and 4-(3,3-dimethyl-1-cyclohexyl)-2,2-dimethyl-3-oxa-1-pentanol (27%) were obtained.

B. p. 40°-75°/20 Pa.

These alcohols were separated by preparative gas phase chromatography and they were both in the form of a racemic mixture of two optically active isomers.

Analytical data:
5-(3,3-dimethyl-1-cyclohexyl)-2-methyl-4-oxa-2-hexanol.

NMR($^1$H,360 MHz): 0.89(s,3H); 0.91(s,3H); 1.08(d,J=6 Hz,3H); 1.20(s,3H); 1.21(s,3H); 3.12(m,2H); 3.32(m,1H) δ ppm.

MS (2 isomers): isomer 1: 228(M+,0), 169(5), 139(25), 123(26), 117(40), 83(74), 73(98), 59(100), 41(29); isomer 2: 228(M+,0), 170(5), 139(21), 123(25), 117(41), 83(69), 73(100), 59(95), 41(26).

4-(3,3-dimethyl-1-cyclohexyl)-2,2-dimethyl-3-oxa-1-pentanol.

NMR($^1$H,360 MHz): 0.86/0.865(2s,3H); 0.90(s,3H); 1.055/1.06(2d,J=6 Hz,3H); 1.135(s,3H); 1.15/1.155(2s,3H); 3.5(s,2H); 3.7(m,1H) δ ppm.

MS (2 isomers): isomer 1: 228(M+,0), 197(10), 139(96), 117(27), 97(25), 83(96), 73(100), 55(42), 41(25); isomer 2: 228(M+,0), 197(10), 139(99), 117(31), 97(24), 83(100), 73(99), 55(50), 41(29).

The mixture of these two alcohols (10 g) in 30 ml of pyridine was treated with propionyl chloride, in a similar manner to that described in Example 2, to yield a mixture of the two desired propanoates (11.2 g; yield: 90%; B. p.: 160°/15 Pa). Said two propanoates were separated by preparative gas chromatography.

Analytical data:
4-(3,3-dimethyl-1-cyclohexyl)-1,1-dimethyl-3-oxapentyl propanoate.

NMR($^1$H,360 MHz): 0.87(s,3H); 0.89(s,3H); 1.05(d,J=6 Hz,3H); 1.08(t,J=7 Hz, 3H); 1.42(s,6H); 2.225(quint.,J=7 Hz,2H); 3.07(hext.,J=7 Hz,1H); 3.48(dd, J$_1$=4.3,J$_2$=9.4 Hz); 3.57(dd,J$_1$=4.3 Hz,J$_2$=9.4 Hz) δ ppm.

MS (2 isomers): isomer 1: 284(M+,0), 210(2), 155(2), 139(18), 129(34), 83(73), 72(79), 57(100), 41(38); isomer 2: 284(M+,0), 210(2), 155(3), 139(18), 129(39), 83(75), 72(73), 57(100), 41(23).

Odor properties: weak odor, less interesting than that of its structural isomer hereinafter.

4-(3,3-dimethyl-1-cyclohexyl)-2,2-dimethyl-3-oxapentyl propanoate.

NMR($^1$H,360 MHz): 0.86/0.865(2s,3H); 0.895/0.90(2s,3H); 1.05/1.055(2d, J=6 Hz,3H); 1.16(t,J=7 Hz,3H); 1.18(s,6H); 2.37(q,J=7 Hz,2H); 3.37(m,1H); 3.94(split s,2H) δ ppm.

MS (2 isomers): isomer 1: 284(M+,0), 197(2), 139(28), 129(78), 83(41), 69(32), 57(100), 41(22); isomer 2: 284(M+,0), 197(2), 139(27), 129(82), 83(43), 69(32), 57(100), 41(22).

Odor properties: described in the introduction.

EXAMPLE 7

Preparation of (1′RS,4RS)-4-(3′,3′-dimethyl-1′-cyclohexyl)-2,2-dimethyl-3-oxapentyl propanoate A solution of 2.5 g of (Z)-2-(3,3-dimethyl-1-cyclohex-ylidene)-1-ethanol [see, for example, A. Gutmann et al., J. Chem. Ecology 7, 919 (1981)] in THF (tetrahydrofuran) was added dropwise, under stirring and argon, to a mixture of LiAlH$_4$ (2 g) and titanocene dichloride (Fluka, 4 spatula tips) in absolute THF at −40°. The reaction mixture was left under stirring at room temperature during the weekend. After washing with water (2 ml), 15% NaOH (2 ml) and again water (6 ml) to hydrolyze, and filtering, 1.9 g of (Z)-3-ethylidene-1,1-dimethylcyclohexane were obtained and used as such in the following step. A small quantity of this product was bulb-to-bulb distilled for analysis:

NMR($^1$H,360 MHz): 0.88(s,6H); 1.54(d,J=6 Hz,3H); 5.24(q,J=6 Hz,1H) δ ppm.

The remainder of this product was added to a 1 molar solution of B$_2$H$_6$ in THF and the mixture was stirred at room temperature for 24 h. There were then added 50 ml of 15% NaOH and 20 ml of perhydrol and stirring was maintained overnight. After extracting with ether, washing with brine, concentrating and distilling (B. p. 100°/20 Pa), 0.7 g of a product whose GC showed that it contained 82% of (1RS,1′RS)-1-(3′,3′-dimethyl-1′-cyclohexyl)-1-ethanol and ∼18% of its (1RS,1′SR) isomer were obtained.

NMR($^1$H,360 MHz): 0.885 and 0.915(2s,6H); 1.15(d,J=6 Hz,3H); 1.85(broad d, 1H); 3.5(m,1H) δ ppm.

NMR($^{13}$C): 20.6(q); 22.1(t); 24.8(q); 28.1(t); 30.7(s); 33.8(q); 39.1(t); 40.9(d); 42.0(t); 72.4(d) δ ppm.

SM: isomer (1RS,1′RS): 154(M+,1), 138(4), 123(30), 112(33), 97(73), 81(39), 69(100), 55(46), 45(33), 41(42); isomer (1RS,1′SR): 154(M+,1), 138(6), 123(30), 112(30), 97(70), 81(37), 69(100), 55(47), 45(30), 41(41).

To 700 mg of the alcohol thus prepared, in solution in 10 ml of toluene, there were added 1 ml of isobutenoxide (BASF) and 5 drops of BF$_3$.(C$_2$H$_5$)$_2$O, under stirring and at −10°. The reaction was allowed to evolve for 4 h at room temperature and the reaction product was then treated in the usual manner. GC of the isolated product showed that around 40% of starting product still remained. The process was therefore repeated and the reaction mixture was allowed to rest overnight. It was then esterified with propionic anhydride in pyridine (1 night) to yield a product containing 84% of (1′RS,4RS)-4-(3′,3′-dimethyl-1′-cyclohexyl)-2,2-dimethyl-3-oxapentyl propanoate and 16% of its (1′SR,4RS) isomer.

MAJOR ISOMER

NMR($^1$H,360 MHz): 0.86 and 0.90(2s,6H); 1.055(d,J=6 Hz,3H); 1.155(t,J=7 Hz, 3H); 1.18(s,6H); 1.82(broad d,1H); 2.36(d,J=7 Hz,2H); 3.37(quint.,J=6 Hz, 1H); 3.95(split s,2H) δ ppm.

NMR($^{13}$C): 174.3(s); 73.9(s); 71.9(d); 70.5(t); 41.8(t); 40.6(d); 39.5(t); 33.7(q); 30.7(s); 29.4(t); 27.7(t); 24.8(q); 24.2(q); 23.9(q); 22.4(t); 19.9(q); 9.2(q) δ ppm.

MS: 284(M+,0), 197(2), 139(27), 129(82), 83(43), 69(32), 57(100), 41(22).

MINOR ISOMER

NMR($^1$H,360 MHz): 0.86 and 0.90(2s,6H); 1.05(d,J=6 Hz,3H); 1.16(t,J=7 Hz, 3H); 1.165/1.175(2s,6H); 1.66(broad d,1H); 2.365(d,J=7 Hz,2H); 3.37(quint.,J=6 Hz,1H); 3.94(split s,2H) δ ppm.

NMR($^{13}$C): 174.3(s); 73.8(s); 71.9(d); 70.5(t); 42.3(t); 40.5(d); 39.5(t); 33.7(q); 30.7(s); 28.4(t); 27.7(t); 24.7(q); 24.2(q); 23.8(q); 22.4(t); 19.7(q); 92(q) δ ppm.

MS: 284(M+,0), 197(2), 139(28), 129(78), 83(41), 69(32), 57(100), 41(22).

Odor properties: pear, musky, ambrette, very nice.

EXAMPLE 8

Preparation of (−)-(1′S,4R)-4-(3′,3′-dimethyl-1′-cyclohexyl)-2,2-dimethyl-3-oxapentyl propanoate A stirred mixture of 146 g (0.93 mol) of (−)-(1R,1′S)-1-(3′,3′-dimethyl-1′-cyclohexyl)-1-ethanol ["(−)-cyclademol", origin: DRT, France; [α]$^{20}$$_D$ = −11°, contained 13% of (1R,1′R) diastereomer], isobutylene oxide (BASF) and 100 ml of cyclohexane was cooled down with an ice bath. To this mixture there was added 1 ml of BF$_3$.(C$_2$H$_5$)$_2$O and, 30 min later, yet another 1 ml of BF$_3$.(C$_2$H$_5$)$_2$O. The cooled mixture was allowed to react for 3 h and was then washed with diluted NaOH, concentrated and distilled on a 50 cm filled column. The product thus obtained (3.8 g), containing 76% of (1′S,4R)-4-(3′,3′-dimethyl-1′-cyclohexyl)-2-methyl-4-oxa-2-ethanol, was heated to 100° together with 10 ml of propionic anhydride, for 6 h, and then distilled in a bulb-to-bulb apparatus to yield 4.4 g of the desired propanoate.

B. p. 130° (bath)/10 Pa; yield: 94%.

α$^{20}$$_D$ = 7.12° (pure).

NMR($^1$H,360MHz): 0.86 and 0.90(2s,6H); 1.05(d,J=6 Hz,3H); 1.16(t,J=7 Hz, 3H); 1.18(s,6H); 1.66(broad d,1H); 2.37(d,J=7 Hz,2H); 3.37(quint.,J=6 Hz, 1H); 3.94(split s,2H) δ ppm.

MS: 284(M+,0), 197(2), 139(28), 129(78), 83(41), 69(32), 57(100), 41(22).

Odor properties: nicely musky and ambrette, pear, floral.

EXAMPLE 9

Preparation of (+)-(1′R,4S)-4-(3′,3′-dimethyl-1′-cyclohexyl)-2,2-dimethyl-3-oxapentyl propanoate 6.2 G of (+)-(1′R,1S)-1-(3′,3′-dimethyl-1′-cyclohexyl)-1-ethanol [prepared from (+)-β-citronellene (Fluka) following the process described by H. R. Ansari, Tetrahedron 29, 1559 (1973); [α]$^{20}$$_D$=11.8°] were reacted with isobutylene oxide (BASF). After distillation, 3.3 g of starting alcohol and 2 g of the desired intermediate product were obtained. The latter was reacted with propionic anhydride to give, after preparative gas chromatography, the desired propanoate.

$\alpha^{20}_D = +6,5°$ (pure).

Odor properties: musky, ambrette, pear.

EXAMPLE 10

Preparation of a Perfuming Composition

A base perfuming composition was prepared by admixing the following ingredients:

| Ingredients | Parts by weight |
|---|---|
| Hexyl acetate | 50 |
| Polymethylol acetate[1] | 1500 |
| TCD acetate[2] | 1500 |
| Methyl cinnamate | 250 |
| 10% * γ-Decalactone | 200 |
| γ-Dodecalactone | 50 |
| 50% * β-Damascone | 250 |
| Isopentyrate[3] | 100 |
| Myroxyde ®[4] | 100 |
| Veloutone[5] | 700 |
| 10% * Bourgeonal[6] | 300 |
| 10% * Lilial ®[7] | 2700 |
| 1% * n-Octanal | 100 |
| Mayol ®[8] | 200 |
| Total | 8000 |

* in dipropylene glycol (DIPG)
[1] tetramethylnonyl acetate; origin: Firmenich SA, Geneva, Switzerland
[2] (tricyclo[5.2.1.0^{2,6}]dec-4-yl)methyl acetate; origin: Firmenich SA, Geneva Switzerland
[3] 1,3-dimethyl-3-butenyl isobutyrate; origin: Firmenich SA, Geneva, Switzerland
[4] mixture of isomers of ocimene epoxide; origin: Firmenich SA, Geneva, Switzerland
[5] 2,2,5-trimethyl-5-pentyl cyclopentanone; origin: Firmenich SA, Geneva, Switzerland
[6] 3-(4-tert-butyl-1-phenyl)propanal; origin: Quest International
[7] 3-(4-tert-butyl-1-phenyl)-2-methylpropanal; origin: L. Givaudan, Vernier, Switzerland
[8] 1-hydroxymethyl-4-isopropyl cyclohexane; origin: Firmenich SA, Geneva, Switzerland When 2000 parts by weight of any one of the preferred compounds of the invention, described in Examples 2 or 6 to 9, were added to this base composition, a new composition was obtained whose odor possessed a clear William pear connotation. In addition, the new composition developed the ambrette note which is typical of the pear and which was totally absent from the base composition odor. This olfactive effect was particularly marked and elegant when the compound described in Example 9 had been added to the base composition.

EXAMPLE 11

Preparation of a perfuming composition for a powder detergent

A base perfuming composition intended for perfuming a powder detergent was prepared by admixing the following ingredients:

| Ingredients | Parts by weight |
|---|---|
| Citronellyl acetate | 200 |
| Amylcinnamic aldehyde | 1000 |
| Hexylcinnamic aldehyde | 2000 |
| 10% * Ambrox ®[1] DL | 100 |
| Isononyl acetate | 200 |
| Verdyl acetate | 400 |
| Verdyl propanoate | 500 |
| 10% * Intreleven aldehyde[2] | 100 |
| 10% * 13-13 Aldehyde[3] | 200 |
| Coumarin | 100 |

-continued

| Ingredients | Parts by weight |
|---|---|
| Lilial ®[4] | 1000 |
| 4-tert-Butyl-cyclohexyl acetate[5] | 1300 |
| Fleuramone ®[6] | 200 |
| 3-Methyl-5-phenyl-1-pentanol[7] | 500 |
| Benzyl salicylate | 700 |
| Tetrahydromuguol[8] | 400 |
| 10% * α-Damascone | 250 |
| Polywood ®[9] | 150 |
| Isoraldeine ®[10] 70 P | 300 |
| Vertofix coeur[11] | 400 |
| Total | 10000 |

* in DIPG
[1] racemic tetramethyl perhydronaphthofuran; origin: Firmenich SA, Geneva, Switzerland
[2] mixture of isomers of undecenal; origin: International Flavors & Fragrances, U.S.A.
[3] n-/i-Tridecanal; origin: Henkel
[4] see Example 10
[5] rich in cis-isomer; origin: Firmenich SA, Geneva, Switzerland
[6] 2-heptyl-1-cyclopentanone; origin: International Flavors & Fragrances, U.S.A.
[7] origin: Firmenich SA, Geneva, Switzerland
[8] isomer mixture; origin: International Flavors & Fragrances, U.S.A.
[9] perhydro-5,5,8a-trimethyl-2-naphthyl acetate; origin: Firmenich SA, Geneva, Switzerland
[10] iso-methyl ionone; origin: L. Givaudan, Vernier, Switzerland
[11] origin: International Flavors & Fragrances, U.S.A.

When 1000 parts by weight of any one of the compounds of the invention described in Examples 2 or 6 to 9 were added to this base composition for a powder detergent, a new composition was obtained whose odor note was more powerful and had more volume, as well as having a clear musky and slightly fruity connotation. This olfactive effect was even more perceptible on textiles washed with a powder detergent perfumed by means of this new composition. The musky connotation of the odor of the new composition according to the invention, which was also present in the odor of the textiles thus washed, was completely different from the musky notes typically imparted by the musky type compounds available on the market. In fact, the compounds of the instant invention made it possible to achieve a fragrant effect which was more powdery-ambrette than the odor effect obtained with the known macrocyclic or indolic compounds having a musky odor. Like in the case of the preceding example, the preferred compound of the invention described in Example 9 provided the best olfactive effect of the type described above.

What we claim is:

1. A compound of formula $$R-O-\underset{R^3}{\overset{R^1}{C}}-\underset{R^4}{\overset{R^2}{C}}-O-\underset{O}{\overset{}{C}}-R^5 \quad (I)$$

wherein R represents a 3,3-dimethyl-1-cyclopentyl or a 3,3-dimethyl-1-cyclohexyl radical, $R^5$ represents a saturated, linear or branched, $C_1$ to $C_3$ alkyl radical and, either $R^1$ and $R^2$ stand each for a hydrogen atom, $R^3$ and/or $R^4$ representing a methyl radical, or $R^3$ and $R^4$ represent each a hydrogen atom, $R^1$ and/or $R^2$ representing then a methyl radical.

2. A mixture of compounds according to claim 1 in the form of isomers of formula

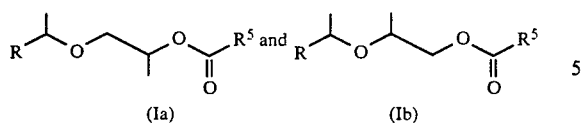

wherein symbols R and R⁵ have the meaning indicated in formula (I).

3. A mixture of compounds according to claim 1 in the form of isomers of formula

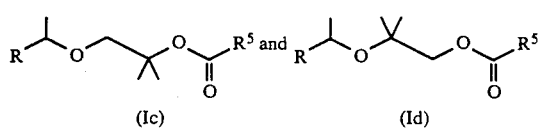

wherein symbols R and R⁵ have the meaning indicated in formula (I).

4. 4-(3,3-Dimethyl-1-cyclohexyl)-2,2-dimethyl-3-oxapentyl propanoate in racemic form or in the form of one of its optically active isomers of formula

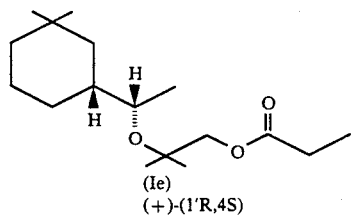

or

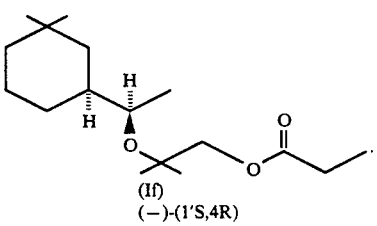

5. 4-(3,3-Dimethyl-1-cyclohexyl)-2-methyl-3-oxapentyl propanoate, 4-(3,3-dimethyl-1-cyclohexyl)-1-methyl-3-oxapentyl propanoate or any mixture of these two compounds.

* * * * *